United States Patent
Foser et al.

(10) Patent No.: US 6,303,059 B1
(45) Date of Patent: Oct. 16, 2001

(54) METHOD OF CONTROLLING AN OVEN

(75) Inventors: Hans-Peter Foser, Balzers (LI); Gottfried Rohner, Altstatten (CH); Wolfram Holand, Schaan (LI); Marcel Schweiger, Chur (CH); Johannes Lorunser, Bludenz (AT); Horst Ulbricht, Eschen (LI)

(73) Assignee: Ivoclar A.G., Schaan (LI)

( * ) Notice: Subject to any disclaimer, the term of this patent is extended or adjusted under 35 U.S.C. 154(b) by 0 days.

(21) Appl. No.: 09/534,934

(22) Filed: Mar. 24, 2000

Related U.S. Application Data

(60) Provisional application No. 60/134,579, filed on May 17, 1999.

(30) Foreign Application Priority Data

Mar. 26, 1999 (DE) ................................................. 199 13 891

(51) Int. Cl.$^7$ .................................................. C04B 33/32
(52) U.S. Cl. .............................. 264/16; 264/19; 264/40.1; 264/40.5

(58) Field of Search ................................ 264/16, 19, 40.1, 264/40.5

(56) References Cited

U.S. PATENT DOCUMENTS 6,136,236 * 10/2000 Boccard et al. ..................... 264/40.1

FOREIGN PATENT DOCUMENTS

| 617064 | 1/1991 | (AU) . |
| 0 438 802 A1 | 7/1991 | (EP) . |

\* cited by examiner

*Primary Examiner*—Christopher A. Fiorilla
(74) *Attorney, Agent, or Firm*—John C. Thompson; Alan S. Korman

(57) ABSTRACT

A method of controlling an oven for producing tooth replacement components. An electric motor moves a piston that acts upon a moldable restoration material. The restoration material is introduced into a muffle oven having an oven hood that can be removed from the muffle. The compactibility curve is established as a function of the type of dental material utilized. Immediately after conclusion of the mold time, the motor is turned off and the oven hood is removed.

16 Claims, 3 Drawing Sheets

METHOD OF CONTROLLING AN OVEN

This application claims benefit of provisional application 60/134,579 filed May 17, 1999

BACKGROUND OF THE INVENTION

The present invention relates to a method of controlling an oven for producing tooth replacement components or dentures, whereby an electric motor moves a piston that acts upon a moldable restoration material that is introduced into a muffle oven having an oven hood that is removable from the muffle.

A method of this type is known from Australian patent 617,064 which also discloses a suitable apparatus, the subject matter of which patent is incorporated herein by reference thereto. With the method of the foregoing patent, an oven for producing a tooth replacement component is controlled in a special manner. A drive mechanism presses upon a piston that deforms a dental material under the effect of heat and presses it into a mold. The mold corresponds to a tooth replacement component and the plastic dental material forms this component upon curing. Whereas with earlier techniques air pockets were frequently formed, and also problems resulted for different geometries of the tooth replacement components, the aforementioned publication taught the improvement of detecting movement parameters of the piston and establishing an alteration of the piston movement velocity as a measure for shutting off the oven.

Even though with these features the quality of the tooth replacement components were significantly improved relative to previously known solutions, a further improvement would be desirable especially for filigree tooth replacement components. A further problem results with the use of in particular lithium disilicate glass ceramics. Although this material is very suitable for the manufacturer of tooth replacement components, it reacts very significantly at high temperatures with the matrix material of the muffle. In order nonetheless to achieve a good surface of the tooth replacement component, it is already known to clean the finished tooth replacement component with aqueous hydrofluoric acid.

However, this known method is not desired for two reasons. For one thing, the handling of aqueous hydrofluoric acid requires special protective measures since hydrofluoric acid is very corrosive. In this connection, the disposal problem is also relevant, since a regeneration directly in a dental lab would be too expensive.

On the other hand, the corrosive etching by the aqueous hydrofluoric acid removes a small amount of material, so that the etched tooth replacement component has slightly smaller dimensions than does the unetched tooth replacement component.

It has furthermore been known for a long period of time to control dental ovens via prescribed programs. With such control methods, a plurality of parameters can be prescribed, whereby for example even complexity of the tooth replacement component can be taken into account. However, the control is affected in particular by the type of heating, and it is theorized that the heating-up curve is very important to the quality of the tooth replacement part that is produced.

It has furthermore already been proposed to allow the pressure or force that acts upon the tooth replacement part to continuously increase at the beginning of the pressing or molding process. However, this measure taken alone leads for large volume tooth replacement components merely to a prolongation of the required molding time.

It is know that a temperature increase of the restoration material during the pressing or molding can shorten the molding time. However, this has a negative effect upon the surface and physical characteristics of the finished tooth restoration component. Therefore, a low temperature and as short a molding time as possible would be ideal, whereby with a practical realization compromises must be made depending upon the type of dental material.

It is therefore an object of the present invention to provide a method of controlling an oven for the production of tooth replacement components as previously described, with such a method being better suitable for different types of tooth replacement parts and in particular permits surfaces of the tooth replacement components to be improved such that the involvement of etching acid can at least be reduced if not entirely eliminated.

SUMMARY OF THE INVENTION

This objective is inventively realized in that a compactibility curve is established as a function of the type of dental material utilized, and after conclusion of the mold time the motor is turned off and the oven hood is removed.

In the following, the present invention is described for a ceramic material, especially for a ceramic blank. However, pursuant to the present invention it is also possible to use polymeric materials, metals and alloys in the form of powder or solid bodies.

Pursuant to the present invention it is particularly expedient that with the inventive features dental replacement components result that have a high quality surface not only for large volume molds but also for filigreed molds. It is particularly advantageous pursuant to the present invention if a compactibility curve is used that has a pressing force that preferably initially rises slowly then achieves a relatively high maximum value, which is maintained, whereby the reduction of the penetration speed of the piston and/or the pressure increase are relied upon as an immediately effective turnoff signal. The relatively strong pressing surprisingly also results in a quite rapid penetration of the dental material into finely branched mold channels and into the mold, so that pursuant to the present invention it is for example readily possible to mold three and multi-element bridges in the filigreed front toothed region of the lower jaw. To the extent that the detected perimeters indicate that the filling process is concluded, the motor is shut off. Depending upon the type of tooth replacement component, it is also possible to institute a retention time, which, however, should also be as short as possible; immediately thereafter, the oven hood is removed so that removal to the cooling process can take place.

Pursuant to one particularly advantageous specific embodiment of the invention, it is proposed that the oven hood be automatically removed. This can be effected in various ways, whereby it is preferred that the oven hood be raised and that the muffle then be pivoted out of the pressing or mold region, so that the muffle can be cooled on a rest surface and if necessary the next muffle with the next prepared tooth replacement components can already be subjected to pressing and molding.

It is particularly expedient pursuant to the present invention to keep the reaction time between the possibly finely branched tooth replacement components and the matrix material as short as possible. In this way, in an inventively surprisingly advantageous manner, matrix materials, for example phosphate-containing matrix materials that are suitable for the high temperature processing, can also be used for new dental ceramics, such as lithium disilicate glass ceramics.

Pursuant to a further, particularly expedient point of view, the occurrence of air cushions can inventively be nearly entirely avoided. Air cushions are inventively avoided by reducing the force of pressure in the beginning for filigreed tooth replacement components, or for large volume tooth replacement components by filling then rapidly without bubbles or pockets, being formed.

It is furthermore particularly expedient pursuant to the present invention to avoid as much as possible the reaction of the matrix material with the ceramic during the temperature dependent viscous flowing process. By minimizing the time of the pressing process, at most a very short reaction time takes place, because due to the relatively high flow velocity the dental material rapidly reaches the objective, where it remains static, so that the possible reaction and possible influence upon the viscosity have no further effects upon the flow process.

Pursuant to another particularly expedient point of view, it is inventively ensured that a bursting or cracking of the matrix material and/or of the muffle is avoided. Since the compactibility curve is adapted to the type of dental material utilized, excess pressure is prevented, whereby the defined control contributes to the prevention of force spikes that could trigger a cracking or bursting of the muffle.

With the inventive method, the cycle time for the production of a tooth replacement component can be reduced, and tests undertaken in conjunction with the present invention have shown that the rejection rate is considerably less.

Further specific features and advantages of the present invention will be described in detail subsequently.

DESCRIPTION OF THE PREFERRED EMBODIMENT

Figure 1:
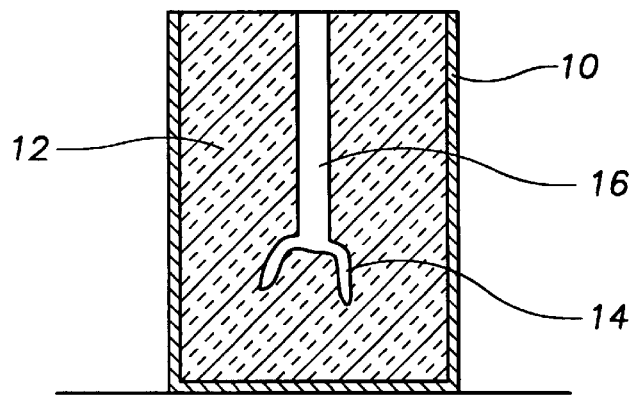
FIG. 1 is a schematic view in the cross section of a prior art apparatus which may be used with this invention.

FIG. 1 shows mold housing 10 in cross section. The mold insert 12 defines a mold cavity 14 and a premolding space 16. The mold cavity 14 is formed in a well known manner with a model of the dental prosthesis to be produced, such as the crown. The mold insert 12 is made of a temperature-resistant material.

The premolding space 16 has a cylindrical form and communicates with the mold cavity 14. Premolding space 16 is defined by the molding insert 12 and has the same smooth surface as the molding cavity 14.

Figure 2:
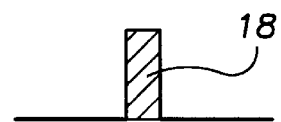
FIG. 2 shows in cross section a raw blank of the mass or material used in the prior art apparatus.

FIG. 2 shows a raw blank 18, shaped as a solid cylinder and having a diameter selected so that it is readily introduced into the premolding space 16 as illustrated in FIG. 1. The volume of blank 18 slightly exceeds the volume of the mold cavity 14 and thus of the dental prosthesis to be produced.

The raw blank 18 is made of a dental material such as a premolded dental ceramic, a metal alloy or a dental plastic. In a modified form of the invention several crowns are produced simultaneously. A plurality of mold cavities 14 are suitably connected with premolding space 16 via appropriate channels and the site of the raw blank 18 is correspondingly larger. When the blank is made of a dental ceramic, it is preferable to mold it in a vacuum and subsequently sinter it so that it is nonporous.

Figure 3:
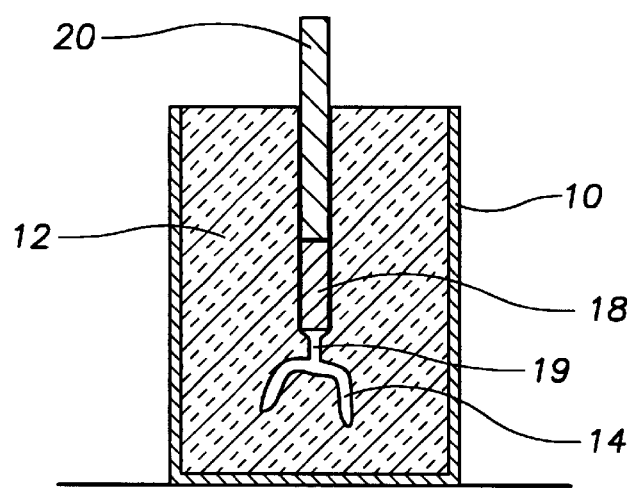
FIG. 3 shows the blank of FIG. 2 inserted in the mold housing shown in FIG. 1, and the cooperating pressure activated piston.
Figure 4:
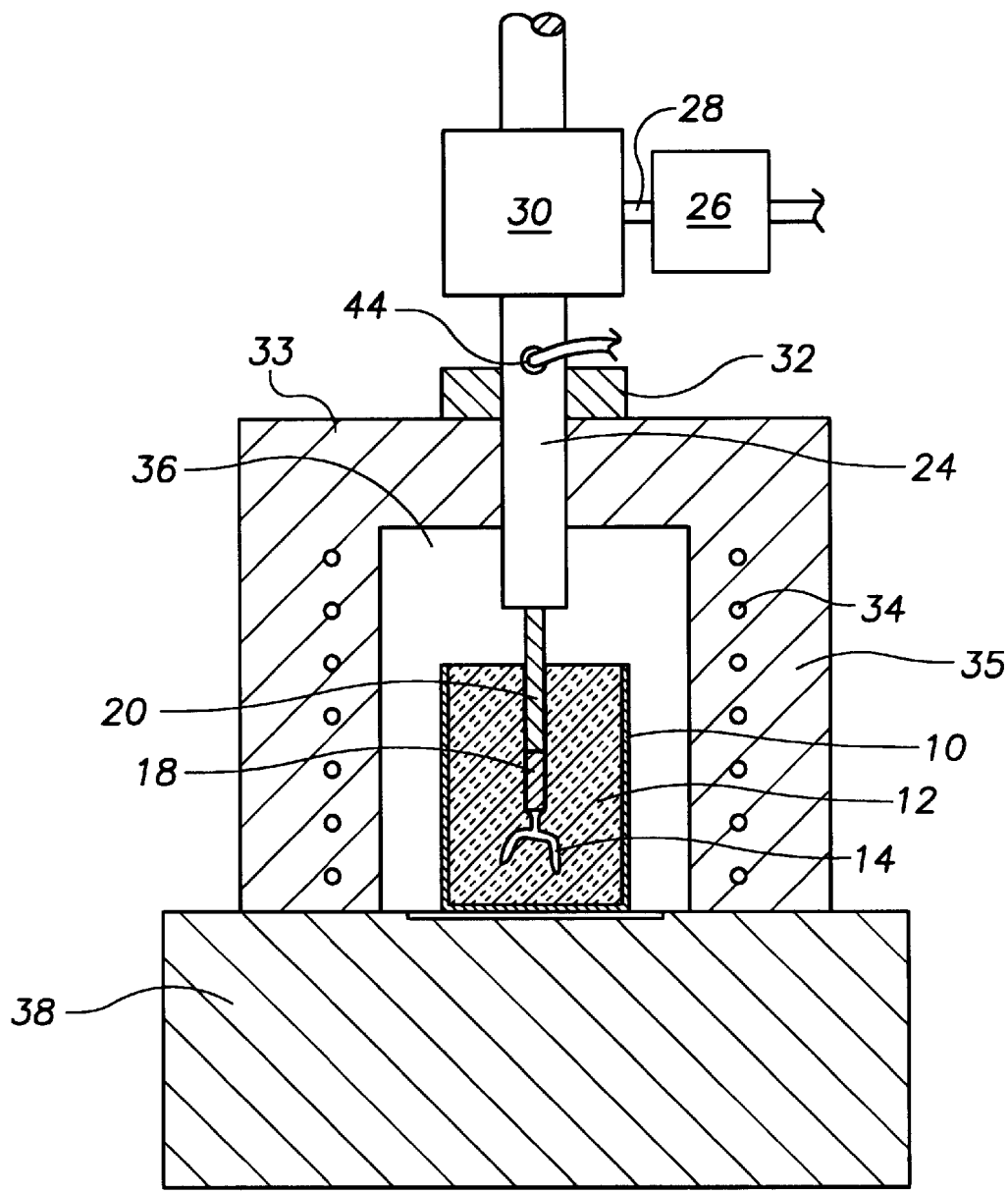
FIG. 4, an enlarged, schematic, cross-sectional view of a mold housing disposed in a furnace including a piston activated in accordance with the principles of this invention.

According to FIG. 3, the raw blank 18 has been advanced into the premolding space 16 so that it is contiguous with a casting channel 19 which is formed either by the material of the molding insert 12 or, as is shown in FIG. 4, as a separate insert. After the blank has been positioned a piston 20 is entered into the premolding space 16. Its diameter is chosen so that it effectively seals with respect to the walls of the premolding space 12 while being readily reciprocal therein. If desired, a known suitably temperature-resistant, special seal can be employed.

As can be seen from FIG. 4, a pressure actuator drives the piston 20 downwardly. In the depicted embodiment, the pressure actuator acts on piston 20 via a piston rod 24. Thus, the unit consisting of housing 10, mold insert 12 and piston 20 is easily removable from the furnace. In accordance with this invention the piston rod 24 is driven by an electric motor 26 having a rotary output shaft 28 which is in turn connected to the piston rod 24 via a suitable mechanism 30 which converts rotary motion to linear motion, such as a rack and pinion mechanism. By operating motor 26 piston rod 24 applies pressure to blank 18 so that it can be deformed and pressed into the mold cavity 14 after it has softened. Since piston rod 24 merely abuts piston 20, a precise alignment of the mold insert 12 is not mandatory. Moreover, no lateral forces are generated because only vertically acting forces can be transferred.

Figure 5:
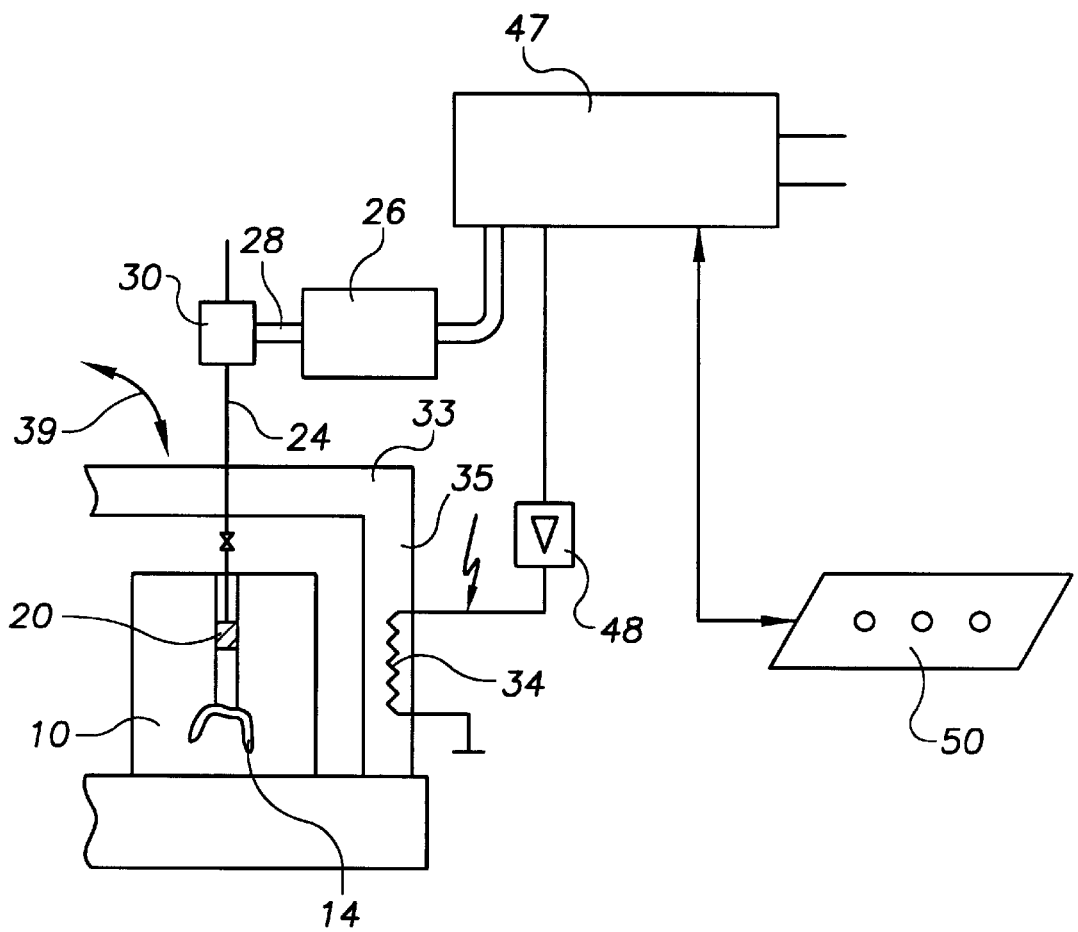
FIG. 5 is a schematic representation of a control system used with this invention.
Figure 6:
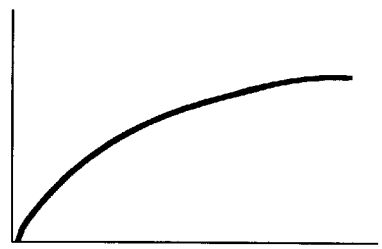
FIG. 6 illustrates a compactibility curve.

Piston rod 24 extends slidably through the top 33 of a furnace and seal 32 is provided so that a vacuum can be maintained in an inner chamber 36 of the furnace which receives housing 10. The furnace includes a heater 34, e.g., a spiral heater in side walls 35. The furnace also has a base 38. A furnace hood is defined by the top wall 33 and the side walls 35 of the furnace. The hood can be raised or tilted off the base 38 as indicated by arrow 39 in FIG. 5. The separation between the base and the hood is sealed.

A control unit 47 is provided. The control unit may be connected to heater 34 via an amplifier 48 such as a thyristor or a relay. The other side of the heater is connected to ground. Thus, unit 47 directly controls heater 34 of furnace.

Control unit 47 is further connected to an input-output console 50. With it the desired heating times, the molding materials used, the desired type of operation (automatic or manual), and other parameters are entered. A pressure sensor 44, such as a strain gauge or the equivalent may be mounted on the piston rod 24. Alternatively, a force sensor of the type shown in copending U.S. patent application Ser. No. 09/391, 708 now U.S. Pat. No. 6,180,922, may be employed.

In a first embodiment, full scale 1:1 models are produced in wax or a thermoplastic polymeric material. This was pinned on a muffle base by means of a round wax wire having a diameter of from 2 to 3 millimeters, so that the wax wires can later serve as sprue runners. Placed around the muffle base was a paper sleeve so that an upwardly open cylindrical mold resulted. The paper sleeve was subsequently filled with an embedding or matrix material that is capable of being poured or cast. Care was taken that the matrix material left no air pockets on the wax or thermoplastic models. Aside from the ends of the sprue runners, the wax or thermoplastic models were completely surrounded by molding or casting material. In the embodiment described, the curing time for the matrix material was one hour. The muffle base and paper sleeve were thereafter easily removed from the hardened casting material.

In this embodiment, in order to harden the matrix material, which is to serve as the mold, and also in order to burn out the wax or the thermoplastic polymer, the mold is subjected to a temperature-time cycle by means of a preheating oven. During this cycle, the muffle was heated to 250° C., and in particular at a heating rate of less than 10° C. per minute, and the oven temperature was kept at standby for 30 minutes.

The mold was subsequently heated up in the preheating oven at temperature gradients of 10° C. per minute to 850° C., and this temperature was held for 90 minutes.

This concluded the manufacture of the mold.

For the inventive molding the still hot mold is transferred into the inventive oven, which was already preheated to 700° C. The mold was lined-up with a blank of the glass ceramic material that was to be worked and with an additional force transferring cylinder of aluminum oxide. The glass ceramic material was IPS Empress 2 of the company Ivoclar AG. The inventive hot molding oven was, initially without pressure but under vacuum, heated up at temperature gradients of 60° C. per minute to 920° C., whereby this temperature was held constant for 20 minutes. The pressure was subsequently applied and led to the viscous flow and to realization of the molding process.

With the first specific embodiment, three parallelepiped rods having dimensions of 1.5 mm×4.0 mm×20 mm were produced in a mold. With this embodiment, the mold pressure was applied without any lag, whereby the force of pressure that was generated by the electric motor and was measured with a force sensor was kept constant at 250N. The conclusion of the mold filling process was detected with a displacement-time measurement. As soon as the pressure or mold piston traveled a distance of less that 0.3 mm within 3 minutes, the progress of the mold time was indicated. Immediately thereafter, the mold was manually removed from the oven and cooled at ambient temperature. In a manner known per se, the mold objects were removed from the mold by streams of abrasive, during the course of which the mold was destroyed.

The thus obtained molded parts were subjected to strength testing via a 3-point test pursuant to ISO 6872. The strength value determined was 373+44 MPa.

With a second specific embodiment, after the conclusion of the process of maintaining the temperature at 920°, as was described in conjunction with the first embodiment, the molding cycle was modified by manually effecting the build-up of force. This method is particularly suitable if very thin mold objects having a complicated geometry must be produced, for example three-element bridges in the front tooth region of the lower jaw. In this embodiment the build-up of force is effected with an increase of 2N, beginning with a starting force of 50N to an end force of 250N. In each mold three parallelepiped rods having the aforementioned dimensions were again formed.

The strength value determined pursuant to ISO 6872 was 371+33 MPa. In comparison for example without a lag in build-up of force there is accordingly evidenced that the delay has no disadvantageous effect upon the strength when Empress 2 was used as the dental material.

In the third specific embodiment, the same parameters apply as with the second embodiment. However, the criterion for the progress of the mold time was modified. With the first two mentioned embodiments, the end criterion was a mold displacement of 0.3 mm per three minutes, and with the third embodiment this end criterion was modified to 0.3 mm mold displacement in one minute. This reduction of the mold time inventively has the particular advantage that the glass ceramic material Empress 2 is no longer in contact for as long a period of time in the hot state with the mold, so that theoretically fewer reactions must result.

As a matter of fact, an electron scan microscope test indicated a clear reduction of the layer thickness of the reaction layer between the dental material and the mold material. On the other hand, already with this embodiment the shortened mold cycle does not have a negative impact upon the strength of the material. Surprisingly, even an increased spot bending strength of 405±40 MPa resulted. It is presumed that with the first and second embodiments the thicker reaction layer weakens the dental material, which would explain the inventive improvement in the strength. In addition, the surface quality was better due to the thinner reaction layer.

In a fourth specific embodiment, a three-element bridge was produced. The mold was produced in the same manner as described in conjunction with the first and second embodiments. A mold channel is formed on the bridge.

After removing the muffle from the preheating oven and placement into the mold oven, which was preheated to 700° C., a mold blank of lithium disilicate glass ceramic was introduced and an aluminum oxide cylinder was installed for transmitting force. The heating up process was undertaken at a temperature gradient of 60° C./minute until a temperature of 920° C. was reached. This temperature was held constant for 20 minutes. A mold or pressure force of 100N was subsequently applied for 20 seconds. The pressure was thereafter continuously increased to 250N, and after 3 minutes the mold oven concluded the molding.

The muffle was removed, cooled, and the bridge was separated from the mold material, in other words, the matrix material. The surface of the bridge was significantly more uniform and more aesthetic than with a comparison molding in a mold oven pursuant to EP-B1-438 801. The molding process elapsed quicker, and the fit of the bridges in the edge region was also significantly better. The reaction phase between the matrix material and the ceramic could be significantly shortened, which was manifested in a reduced thickness of the reaction layer. The bridge was treated for 10 minutes with aqueous hydrofluoric acid in an ultrasonic bath and was thereafter finished in a conventional manner.

The present invention is, of course, in no way restricted to the specific disclosure of the specification, but also encompasses any modifications within the scope of the appended claims.

What is claimed is:

1. A method of controlling an oven for producing tooth replacement components in a muffle oven having an oven hood that is removable from a muffle thereof, including the steps of:

a) introducing a moldable restoration material into said oven;

b) moving a piston with an electric motor to act on said restoration material;

c) establishing a compactibility curve as a function of the type of dental material utilized;

d) after conclusion of a mold time turning said motor off;

e) maintaining a vacuum in the furnace during steps b–d; and f) removing said oven hood.

2. A method according to claim 1, wherein upon initiation of plastification said compactibility curve rises, and wherein an end force of pressure is greater than 200N.

3. A method according to claim 2, wherein said end force of pressure is a maximum of 300N.

4. A method according to claim 1, which includes the further steps of measuring a force of pressure, and using as a turnoff criterion for the pressing or molding process an increase of current consumption of said electric motor, which indicates a conclusion of said pressing process.

5. A method according to claim 4, which includes the step of determining an end of said force of pressure in the case of a pressure path of less than 0.5 mm within less than 2 minutes.

6. A method according to claim 5, wherein said end of said force of pressure is determined in the case of a pressure path of less than 0.1 mm within about one minute.

7. A method according to claim 1, wherein prior to initiation of a pressing or molding process, especially with a positive model of a tooth replacement component, the magnitude of the tooth replacement part that is to be produced on the one hand, and the thickness of the thinnest molding channels within the tooth replacement component on the other hand, are determined, and said compactibility curve is established as a function of the determined values thereof.

8. A method according to claim 1, wherein said electric motor limits a force of pressure to a value that is below a force of molding, and wherein said force of molding can be set as a function of the material of said tooth replacement components.

9. A method according to claim 1, wherein a force sensor is provided for measuring a force of pressure applied by said electric motor via said piston onto the dental material, and wherein said electric motor is controlled by said force sensor via a control mechanism.

10. A method according to claim 1, which includes the step of determining a force of pressure and a displacement of said piston, wherein said compactibility curve is realized, accompanied by control of displacement and time, pursuant to prescribed parameters as a function of a selection of the dental material and of the geometry of a tooth replacement component.

11. A method according to claim 1, wherein said electric motor is a stepper motor, and which includes the steps of detecting an increase of force with each step of said stepper motor via a force sensor, and utilizing an increase of force of pressure as a turn-off criterion.

12. A method according to claim 1, which includes the steps of providing said oven hood with a displacement and/or pivot mechanism, and upon conclusion of a pressing or molding time, and if desired after a retention time, automatically raising and/or pivoting away said oven hood.

13. A method according to claim 1, wherein said electric motor is embodied as a stepper motor, and said oven hood is removed only after a retention time following said conclusion of said mold time.

14. A method according to claim 1, which includes the step of utilizing known, essentially cylindrical, prefabricated blanks as said moldable restoration material.

15. A method according to claim 1, wherein said compactibility curve is optimally adapted to said material that is to be molded, whereby a maximum force of pressure is set such that it is safely below a force of pressure that would lead to breaking or bursting of a matrix muffle.

16. A method according to claim 15, wherein said moldable material is a glass ceramic.

* * * * *